United States Patent [19]

Weibel et al.

[11] Patent Number: 5,750,140

[45] Date of Patent: May 12, 1998

[54] TRANSDERMAL DELIVERY OF TIAGABINE

[75] Inventors: Helle Weibel, Hillerød; Peter Bonne Eriksen, Værløse, both of Denmark

[73] Assignee: Novo Nordisk A/S, Bagsvaerd, Denmark

[21] Appl. No.: 440,155

[22] Filed: May 12, 1995

[30] Foreign Application Priority Data

May 20, 1994 [DK] Denmark ................................ 0577/94

[51] Int. Cl.$^6$ ............................ A61M 37/00; A61K 9/70
[52] U.S. Cl. ............................ 424/449; 424/486; 604/304
[58] Field of Search ................................ 424/486, 449; 604/304

[56] References Cited

FOREIGN PATENT DOCUMENTS

| 2 105 990 | 4/1983 | United Kingdom . |
|---|---|---|
| WO 91/09592 | 7/1991 | WIPO . |
| WO 92/17473 | 10/1992 | WIPO . |

OTHER PUBLICATIONS

Abstract JP 3058941 A.

*Primary Examiner*—Edward J. Webman
*Attorney, Agent, or Firm*—Steve T. Zelson; Elias J. Lambiris

[57] ABSTRACT

A transdermal delivery system containing tiagabine or its pharmaceutically acceptable salts or esters is disclosed. The delivery system is useful in the treatment of epilepsy.

10 Claims, No Drawings

TRANSDERMAL DELIVERY OF TIAGABINE

This invention relates to transdermal drug delivery. More particularly, this invention relates to anti-epileptic drug delivery and still more particularly, but without limitation thereto, this invention relates to the transdermal delivery of N-(4,4-di(3-methylthien-2-yl)-but-3-enyl)nipecotic acid and pharmaceutically acceptable derivatives thereof at therapeutically effective rates.

Epilepsy is the most common serious neurological disorder, occurring at a similar rate throughout the world.

As the onset of epilepsy occurs most frequently during childhood and since antiepileptic drugs often may be taken for a long period of time leading to possible adverse effects it is of great importance to choose the relevant route of delivery.

The transdermal route for delivery of drugs provides many advantages such as noninvasive drug delivery, no first pass effect, lower dose and better compliance for patients with dosing problems as to conventional dosing forms, i.e. tablets or capsules.

The transdermal route will therefore be a good choice in the long term treatment of patients suffering from epilepsy and more specifically in the treatment of children suffering from epilepsy. Transdermal systems for delivering a wide variety of drugs or other agents are described in f.inst. U.S. Pat. No. 4,978,532 and in PCT publication W091/09592.

U.S. Pat. No. 5,010,090 discloses N-(butenyl substituted) azaheterocyclic carboxylic acids, which compounds potentiate GABA-ergic neurotransmission and therefore said compounds are valuable in the treatment of epilepsy.

N-(4,4-di(3-methylthien-2-yl)-but-3-enyl)nipecotic acid, hydrochloride is specifically disclosed in U.S. Pat. No. 5,010,090.

In C. Braestrup et. al., Int. Congr. Ser.-Exerpta Med., 1987, 750 (Pharmacology), 125-8 the various isomers of N-(4,4-di(3-methyithien-2-yl)-but-3-enyl) nipecotic acid, hydrochloride are disclosed. The R-isomer of N-(4,4-di(3-methylthien-2-yl)-but-3-enyl) nipecotic acid is referred to by its generic name of tiagabine in the present invention.

Tiagabine has been found useful in the treatment of epilepsy. The present invention is directed to a drug delivery dosage form for transdermal administration of tiagabine to a patient, preferably a child, suffering from epilepsy, which comprises a matrix which contains tiagabine and an effective permeation enhancer.

An investigation performed by Silvestri & Cannon (unpublished study) showed that a transdermal patch for delivery of tiagabine would not be feasible due to lack of permeability. In vitro diffusion experiments were performed to evaluate the permeability of tiagabine hydrochloride through human cadaver skin using a Franz diffusion cell system. pH 6.4 and 10.4 buffers were chosen as the appropriate donor and receptor fluids and under these conditions it was concluded that delivery of more than 10 mg of Tiagabine per day in a transdermal patch is not feasible.

It has now surprisingly been found that therapeutically effective amounts of tiagabine can be administered transdermally by incorporating of the drug in a matrix suitable for transdermal delivery which matrix contains an effective permeation enhancer.

Zwitterionic drugs have poor absorption through intact skin due to their rather large dipole moments and their resulting low lipid solubility. Zwitterionic drugs cannot be made nonionic. At all pH-values, at least one ionic group is present. It would not be expected that one could achieve a suitable flux of a zwitterion through the skin to make transdermal administration thereof practical.

Surprisingly, it was possible by use of selected enhancers to administer tiagabine through human skin in acceptable amounts, despite the fact that tiagabine is known to be a zwitterion.

The permeation enhancer is selected from those known by man skilled in the art preferably those enhancers selected from a) saturated or unsaturated fatty acids, preferably $C_{14}$–$C_{22}$-acids, more preferably $C_{18}$-acids, specifically oleic acid or esters thereof in propylene glycol, b) specific compounds such as bisabolol(6-methyl-2-(4-methyl-3-cyclohexen-1-yl)-5-hepten-2-ol) in ethanol, cineol(1,3,3-trimethyl-2oxabicyclo[2. 2.2]octane) in ethanol, hydroxypropyl-β-cyclodextrin (HPCD) or decylmethylsulfoxid (DMS).

Furthermore, the enhancement can be increased by selection of pharmaceutically acceptable alkyl esters of tiagabine of ionpairs between tiagabine and organic acids.

An enhancement of the permeation according to the invention is also obtained by creation of an ion pair between the nitrogen-atom in tiagabine and a suitable organic acid such as oleic acid or salicylic acid.

Furthermore, a better permeation is obtained by $C_{1-6}$-alkyl-ester of tiagabine. More particular, an enhancement of permeation were obtained with the ethylester of tiagabine.

The transdermal delivery systems of the present invention include an effective amount of tiagabine, its salts, ion pairs or esters.

In particular the present invention includes the following salts and hydrates thereof: Acetate, benzoate, fumarate, phosphate, malate, maleate, mandelate, mesylate, lactate, salicylate, sulphate, tartrate, succinate and hydrochloride.

Drugs can be delivered into the systemic circulation via the human skin membrane with low daily doses because first pass hepatic metabolism is avoided (Todd P. A. & Goa K. L., Drugs 40(4): p. 583–607 (1990)). This may be convenient because low-dose forms may avoid some of the side effects of higher dose oral therapy.

The daily dose of tiagabine is from 0.1–10 mg/kg body weight, preferably from 0.3–2 mg/kg body weight.

By the term effective amount it is understood that such an amount is sufficient to provide the desired result, that is, treatment of epilepsy. In this regard, transdermal delivery systems deliver an amount of from about 0.01 mg to about 10 mg per kg. body weight per day of tiagabine or its salts or esters.

DETAILED DESCRIPTION OF PREFERRED PATCH EMBODIMENTS

A preferred embodiment of the present invention is a microsealed, transdermal tiagabine pad having-a backing which is impervious to tiagabine absorption and transport, and a silicon polymer matrix affixed thereto, the silicone polymer matrix being of cross-linked silicone rubber having from about 10 to 200 μm microsealed compartments being formed by in situ cross-linking of the silicone rubber after it is mixed with the hydrophillic solvent system containing the tiagabine and the hydrophobic solvent system which enhances tiagabine transport and dispersion, the tiagabine being diffusible through the biologically acceptable silicon polymer matrix at a therapeutically effective constant rate when the microsealed tiagabine pad is affixed to the skin, said hydrophobic solvent being non-diffusible through the biologically acceptable polymer matrix.

A most preferred embodiment of the present invention is a microsealed, transdermal tiagabine delivery device comprising a biologically acceptable silicone polymer matrix and wherein the biologically acceptable silicone polymer matrix has microsealed compartments distributed throughout, said microsealed compartments containing from 6 to 22 weight percent of 10 weight percent tiagabine mixed with lactose in a hydrophillic solvent system comprising enhancer mixture, and from 5 to 15 weight percent of a hydrophobic solvent selected from the group consisting of mineral oil, oils derived from coconut oil or mixtures thereof. Representative coconut oil derivatives include isopropyl palmitate and miglyol oil. The microsealed compartments are formed by in situ cross-linking of the liquid silicone polymer after it is emulsified with the hydrophillic solvent system containing the tiagabine and the enhancer mixture.

Generally speaking, to prepare the transdermal tiagabine pad of the present invention, a saturated solution of a 10 percent tiagabine-lactose mixture is prepared in a suitable hydrophillic enhancer mixture. An excess amount of the tiagabine-lactose mixture is maintained in this preparation to obtain a uniform paste after manual or mechanical mixing for approx. 5-10 min. This uniform paste is added to the silicone elastomer, i.e. MDX 4-4210 elastomer, (Dow Corning, Midland, Mich.) along with the required amount of a hydrophobic solvent or a similar solvent mixture, such as mineral oil, isopropyl palmitate, or a mixture thereof. All of these ingredients are mixed from 5 to 15 min. in a low shear, explosion-proof mixing vessel maintained under vacuum. A polymeric monomer is added to the mixture. The polymerizing catalyst is added and mixing is continued under vacuum from about 15 to 30 min. The final mixture is viscous, and is poured, with the aid of mixing equipment, into clean, dry stainless steel plates. In the case of 2×4 cm pads, suitable amounts of the final mixture are poured into 12" by 12" stainless steel plates fitted with a frame of a desired thickness ranging from 5.0 mm to 1.2 mm. A suitable material, such as aluminium foil, is placed on the poured material and top plates having the same dimensions as the bottom plates, but without frames, are pressed to fill the molds with the polymerizing formulation. The molds are secured in place with screws in four corners and placed in an air circulating oven at about 60° C. After two hours, the molds are removed, cooled, and the cured pad material adhering to the aluminium foil is pulled off, cut into suitable size pads, e.g. 2×4 cm with aluminium foil backing. The pads are then stored in air tight containers.

The invention will now be described in more detail.

EXAMPLE 1

The effect of various types of effective permeation enhancers on tiagabine is illustrated in the following way:

Permeation Procedure

Franz glass diffusion cells were used (Franz, T. J.: Curr. Probl. Dermatol., 1978: 7; 58–68).

Experiments were performed on Caucasian abdominal or breast skin obtained after surgery and kept at −20° C. for not more than three months. After thawing, the skin samples were stripped off their adipose tissue with a razor, giving a skin membrane of epidermis and dermis of a thickness of approximately 2 mm.

The human skin membrane was enclosed in the glass chambers with ground faces (diffusing area 1.77 cm$^2$). A clamp was used to keep the chambers together. To assure that the stratum corneum membrane was intact, one ml of 0.05M phosphate buffer pH 7.4 was applied on the epidermal side of the skin, while the lower part of the skin was in contact with the same medium.

After the skin was allowed to equilibrate at 32° C. for one hour, the capacitance was measured with a Lutron DM 6023 Capacitance meter. Values below 0.150 μF. indicated that the stratum corneum was intact. After the capacitance experiment was performed, the phosphate buffer from donor and receptor chamber was removed. The epidermal side of the skin was exposed to ambient laboratory conditions, while the lower part of the skin was in contact with receptor medium, consisting of 0.05M phosphate buffer pH 7.4 with 0.05 mg/ml gentamycin sulphate, 32° C. Before application of donor phase, the receptor medium was allowed to equilibrate with the skin for one hour.

The donor phases were made of suspensions of tiagabine in media consisting of different permeation enhancers, cf. Table 1. To prepare the donor phases, tiagabine was added to the solution containing the enhancer, and after stirring at room temperature for 72 hours, the solution were saturated with tiagabine. 500 μl of the donor phase was applied on the epidermal side of the skin, and the experiment was performed with occlusion. After filtering through a Millipore filter 0.22 μm, the concentration of tiagabine in the donor phases was detected by using HPLC.

In order to investigate, if possible substances in the skin may appear on the chromatogram by using the HPLC-method, a solution without tiagabine was applied on the epidermal side of the skin of one permeation cell.

To evaluate the differences in permeability of tiagabine between the skin from different women, a standard solution containing water saturated with tiagabine was investigated as a donor phase on skin from every woman.

At appropriate intervals, samples were taken from the receptor phase and replaced by fresh receptor solution in order to keep sink-conditions.

The amount of tiagabine in the receptor solution was determined using HPLC.

Results

The flux (J), representing the tiagabine permeation rate is given as (see: Scheuplein, R. J. & Blank, I. H.:Physiol. Rev. 1971: 51; 702–747)

$$J = \frac{dq/dt}{A} \quad [1]$$

in which dq/dt is the steady-state rate of permeation or appearance of solute in the receptor solution (μg/hour), and A is the area of the exposed skin (1.77 cm$^2$). The flux was calculated from equation 1 and the slopes of the linear portions of the plots of q/t.

The mean value and the standard deviation were calculated of the flux J of the replicates.

The in vitro data expresses the expected doses deliverable by transdermal patches preferable in a size of 5–100 cm$^2$, more preferably in a size of 30 cm$^2$.

Amount delivered per day=J·A

J=flux (μg·cm$^{-2}$·24h$^{-1}$)

A=area of a patch (30 cm$^2$)

The results obtained appears from the following Table 1:

TABLE 1

RESULT OF DIFFUSION CELL MEASUREMENTS

| Skin sample | Formulation, tiagabine and enhancer | Conc. of tiagabine in donor phase mg/ml | Flux (J) of tiagabine $\mu g \cdot cm^{-2} \cdot 24h^{-1}$ x ± s.d. | **Delivered mg per day |
|---|---|---|---|---|
| A | Phosphate buffer pH = ~7.5 | 3 | 7.4 ± 3.2 | 0.22 |
|  | standard* | 25 | 15.5 ± 8.5 | 0.47 |
| B | Glycerol | 51 | n.p. | 0 |
|  | standard* | 25 | 73.2 ± 17.4 | 2.20 |
| C | Propylene Glycol | 147 | n.p. | 0 |
|  | standard* | 25 | 39.5 ± 13.2 | 1.19 |
| D | Poly Ethylene Glycol 400 | 120 | n.p. | 0 |
|  | standard* | 25 | 5.6 ± 0.44 | 0.17 |
| E | 10% Oleic Acid in Propylene Glycol | 153 | 224 ± 67 | 6.72 |
|  | 10% Ethyl Oleat in Propylene Glycol | 179 | 58.0 ± 22.4 | 1.74 |
|  | Standard* | 27 | 40.2 ± 22.1 | 1.21 |
| F | 10% Bisabolol in Ethanol/water (66/33 v/v) | 330 | 227 ± 32.8 | 6.81 |
|  | 10% Cineol in Ethanol/water (66/33 v/v) | 306 | 40.1 ± 11.3 | 1.20 |
|  | Ethanol/water (66/33 v/v) | 296 | 8.2 ± 2.2 | 0.25 |
| G | 10% Decyl Methyl sulfoxid in Ethanol/water (33/66 v/v) | 364 | 71.5 ± 21.8 | 2.15 |
|  | 10% HPCD in Ethanol/water (33/66 v/v) | 243 | 5.4 ± 1.1 | 0.16 |
|  | Ethanol/water (33/66 v/v) | 300 | 7.2 ± 1.5 | 0.22 | x: Mean value
s.d.: Standard deviation
n.p.: No permeation
*: Standard solution containing water saturated with tiagabine
**: Amount delivered from a 30 cm² patch.

EXAMPLE 2

Tiagabine-patch with oleic acid (E)

A 10 percent tiagabine-lactose mixture (55 g) was mixed for about 5 min. with 25.0 g of 10 percent (v/v) oleic acid solution in propylene glycol. A uniform paste of the above mixture was added to 157.5 g of MDX 4-4210 silicone elastomer (Dow Corning, Midland, Mich.). Upon mixing for about 10 min. under initial deaeration, a uniform dispersion was obtained in a low shear mixer. To this dispersion was added 12.5 g of the curing agent for the MDX 4-4210 elastomer and mixing was continued for another 15 min. The final mixture was poured into 12"×12" stainless steel plates with a 5 cm frame to hold the curing material. Aluminum foil (12"×12") was placed into each plate and pressed into the mold with a 12"×12" stainless steel plate. The molds were secured with screws affixed on four corners and placed in an air-circulating oven at about 60° C. for approx. two hours. Upon cooling, the polymer matrix, adhering to the aluminum foil as a backing, was removed from the molds and cut into 1.6×3.2 cm pads which were stored in air tight containers until use.

EXAMPLE 3

Tiagabine-patch with bisabolol (F)

A 10 percent tiagabine-lactose mixture (55 g) was mixed for about 5 min. with 25.0 g of 10 percent bisabolol in ethanol/water (66/33% v/v). A uniform paste of the above mixture was added to 157.5 g of MDX 4-4210 silicone elastomer (Dow Corning, Midland, Mich.). Upon mixing for about 10 min. under initial deaeration, a uniform dispersion was obtained in a low shear mixer. To this dispersion was added 12.5 g of the curing agent for the MDX 4-4210 elastomer and mixing was continued for another 15 min. The final mixture was poured into 12"×12" stainless steel plates with a 5 cm frame to hold the curing material. Aluminum foil (12"×12") was placed into each plate and pressed into the mold with a 12"×12" stainless steel plate. The molds were secured with screws affixed on four corners and placed in an air-circulating oven at about 60° C. for approx. two hours. Upon cooling, the polymer matrix, adhering to the aluminum foil as a backing, was removed from the molds and cut into 1.6×3.2 cm pads which were stored in air tight containers until use.

EXAMPLE 4

Tiagabine-patch with decyl methyl sulfoxid (G)

A 10 percent tiagabine-lactose mixture (55 g) was mixed for about 5 min. with 25.0 g of 10 percent decyl methyl sulfoxide in ethanol/water (33/66% v/v). A uniform paste of the above mixture was added to 157.5 g of MDX 4-4210 silicone elastomer (Dow Corning, Midland, Mich.). Upon mixing for about 10 min. under initial deaeration, a uniform dispersion was obtained in a low shear mixer. To this dispersion was added 12.5 g of the curing agent for the MDX 4-4210 elastomer and mixing was continued for another 15 min. The final mixture was poured into 12"×12" stainless steel plates with a 5 cm frame to hold the curing material. Aluminum foil (12"×12") was placed into each plate and pressed into the mold with a 12"×12" stainless steel plate. The molds were secured with screws affixed on four corners and placed in an air-circulating oven at about 60° C. for approx. two hours. Upon cooling, the polymer matrix, adhering to the aluminum foil as a backing, was removed from the molds and cut into 1.6×3.2 cm pads which were stored in air tight containers until use.

We claim:

1. A transdermal delivery system comprising one or more permeation enhancers and a compound selected from the group consisting of tiagabine, pharmaceutically acceptable salts or pharmaceutically acceptable $C_{1-6}$-alkylesters thereof and ionpairs of tiagabine and salicylic or oleic acid, wherein the penetration enhancer is selected from the group consisting of saturated and unsaturated fatty acids and esters thereof in propylene glycol, bisabolol in ethanol/water, cineol in ethanol/water, hydroxypropyl-β-cyclodextrin in ethanol/water or decylmethylsulfoxide in ethanol/water and the ratio by weight of the compound to the one or more permeation enhancers is 1:1.

2. The delivery system of claim 1, wherein the permeation enhancer is oleic acid in propylene glycol.

3. The delivery system of claim 1, wherein the permeation enhancer is bisabolol in ethanol/water.

4. The delivery system of claim 1, wherein the permeation enhancer is decyl methyl sulfoxid in ethanol/water.

5. The delivery system of claim 1, wherein the compound is a pharmaceutically acceptable salt or ester selected from the group consisting of acetate, benzoate, fumarate, phosphate, malate, maleate, mandelate, mesylate, lactate, salicylate, sulphate, tartrate, succinate, hydrochloride and hydrates.

6. The delivery system of claim 1, wherein the permeation enhancer and the compound are dispersed in a matrix.

7. The delivery system of claim 1, wherein the compound is present in an amount of from about 0.01 mg to about 10 mg per kg. body weight per day.

8. A method of enhancing the penetration of a compound through human and non-human skin and membranes, comprising adding a penetration enhancer to the compound, wherein the compound is selected from the group consisting of tiagabine, pharmaceutically acceptable salts and pharmaceutically acceptable $C_{1-6}$-alkylesters thereof and ionpairs of tiagabine and salicylic or oleic acid and wherein the penetration enhancer is selected from the group consisting of saturated and unsaturated fatty acids and esters thereof in propylene glycol, bisabolol in ethanol/water, cineol in ethanol/water, hydroxypropyl-$\beta$-cyclodextrin in ethanol/water or decylmethylsulfoxide in ethanol/water, wherein the ratio by weight of the compound to the permeation enhancer is 1:1.

9. A method of treating epilepsy comprising transdermally administering a permeation enhancer and an effective amount of a compound, wherein the compound is selected from the group consisting of tiagabine, pharmaceutically acceptable salts and pharmaceutically acceptable $C_{1-6}$-alkylesters thereof and ionpairs of tiagabine and salicylic or oleic acid, wherein the penetration enhancer is selected from the group consisting of saturated and unsaturated fatty acids and esters thereof in propylene glycol, bisabolol in ethanol/water, cineol in ethanol/water, hydroxypropyl-$\beta$-cyclodextrin in ethanol/water or decylmethylsulfoxide in ethanol/water and the ratio by weight of the compound to the permeation enhancer is 1:1.

10. The method of claim 9, wherein the compound is delivered in an amount of from about 0.01 mg to about 10 mg per kg. body weight per day.

* * * * *